(12) United States Patent
Spencer (10) Patent No.: US 8,923,631 B2
(45) Date of Patent: Dec. 30, 2014

(54) METHOD AND DEVICE FOR CLASSIFYING VASCULAR OBJECTS USING CLASSIFICATION TREES EVALUATED ON A GRAPHICS PROCESSING UNIT

(75) Inventor: Jason Spencer, Rocklin, CA (US)

(73) Assignee: Volcano Corporation, San Diego, CA (US)

( * ) Notice: Subject to any disclaimer, the term of this patent is extended or adjusted under 35 U.S.C. 154(b) by 132 days.

(21) Appl. No.: 13/588,193

(22) Filed: Aug. 17, 2012

(65) Prior Publication Data

US 2013/0044924 A1 Feb. 21, 2013

Related U.S. Application Data

(60) Provisional application No. 61/524,705, filed on Aug. 17, 2011.

(51) Int. Cl.
  G06K 9/68 (2006.01)
  G06K 9/00 (2006.01)
  A61B 8/14 (2006.01)
  G06K 9/62 (2006.01)
  A61B 8/08 (2006.01)
  A61B 8/12 (2006.01)

(52) U.S. Cl.
  CPC .......... *A61B 8/5223* (2013.01); *G06K 9/00986* (2013.01); *A61B 8/12* (2013.01); *G06K 9/6282* (2013.01)
  USPC ............ 382/226; 382/128; 600/463; 600/425

(58) Field of Classification Search
  CPC ... G06K 9/6282; G06K 9/00986; A61B 8/12; A61B 5/0066; A61B 2019/5234
  USPC ......................................................... 382/128
  See application file for complete search history.

(56) References Cited

U.S. PATENT DOCUMENTS

| | | | |
|---|---|---|---|
| 6,200,268 | B1 | 3/2001 | Vince et al. |
| 2004/0152983 | A1 | 8/2004 | Vince et al. |
| 2006/0241486 | A1 | 10/2006 | Nair et al. |
| 2007/0083111 | A1 | 4/2007 | Hossack et al. |
| 2009/0093980 | A1 | 4/2009 | Kemp et al. |
| 2010/0094800 | A1* | 4/2010 | Sharp .............................. 706/55 |

OTHER PUBLICATIONS

Garcia-Garcia, Hector M., Marco A. Costa, and Patrick W. Serruys. "Imaging of coronary atherosclerosis: intravascular ultrasound." European heart journal 31.20 (2010): 2456-2469.*
Jang, Ik-Kyung, et al. "Visualization of coronary atherosclerotic plaques in patients using optical coherence tomography: comparison with intravascular ultrasound." Journal of the American College of Cardiology 39.4 (2002): 604-609.*
Nair, Anuja, et al. "Coronary plaque classification with intravascular ultrasound radiofrequency data analysis." Circulation 106.17 (2002): 2200-2206.*

(Continued)

*Primary Examiner* — Nirav G Patel
*Assistant Examiner* — Geoffrey E Summers
(74) *Attorney, Agent, or Firm* — Haynes and Boone, LLP (57) ABSTRACT

Methods and devices for optimizing classification tree evaluation for online and real-time characterization of tissue by using GPUs are disclosed that give a significant improvement in run time compared to data decomposition. The methods and devices use a parallel algorithm designed for single instruction, multiple data (SIMD) architectures commonly found in GPUs. Various optimizations and their effects are also disclosed.

18 Claims, 5 Drawing Sheets

(56) References Cited

OTHER PUBLICATIONS

Nottingham, Alastair, and Barry Irwin. "Parallel packet classification using GPU co-processors." Proceedings of the 2010 Annual Research Conference of the South African Institute of Computer Scientists and Information Technologists. ACM, 2010.*

International Searching Authority/Korean Intellectual Propoerty Office, "Notification of Transmittal of the International Search Report and the Written Opinion of the International Searching Authority, or the Declaration," for PCT/US2012/051291, mailed Feb. 1, 2013, 10 pages.

Jason Spencer, "Speculative Parallel Evaluation of Classification Trees on GPGPU Compute Engines" Aug. 15, 2011, 22 pages.

* cited by examiner

METHOD AND DEVICE FOR CLASSIFYING VASCULAR OBJECTS USING CLASSIFICATION TREES EVALUATED ON A GRAPHICS PROCESSING UNIT

CROSS-REFERENCE TO RELATED APPLICATIONS

The present application claims priority to and the benefit of U.S. Provisional Patent Application No. 61/524,705, filed Aug. 17, 2011, which is hereby incorporated by reference in its entirety.

FIELD

The present disclosure relates generally to the field of tissue characterization used to diagnose and treat maladies in humans and more specifically to tissue characterization used in conjunction with in intravascular ultrasound (IVUS) or optical coherence tomography (OCT) systems.

BACKGROUND

Methods and systems for characterizing tissue including tissue types within tissue are known (See, for example, U.S. Pat. Nos. 6,200,268; 6,381,350; 7,074,188; 7,175,597; 7,215,802; 7,359,554; 7,463,759; 7,627,156; 7,789,834; 7,874,990; 7,899,224; 7,927,275; 7,940,969; and 7,978,916; each of which is hereby incorporated by reference in its entirety). In these previous methods and systems, tissue is scanned with an imaging device, (e.g., an intravascular ultrasound (IVUS) or optical coherence tomography (OCT) device) and backscatter signal data is collected. Histology images are prepared and digitized which correspond to the scanned vascular sections. A tissue type is selected on the histology image and its coordinates are mapped to a corresponding location on the IVUS or OCT image constructed from the backscatter signal. The image location is then translated to the corresponding signal section of the raw backscatter signal. Frequency analysis is performed on the signal section to determine its signal properties. The signal properties are correlated to the selected tissue type of the histology image and stored in a tissue characterization database. The process is then repeated for all tissue types and other tissue types found within tissue and stored in the database. The components of tissue such as tissue can be identified directly from the raw backscatter signal by matching its signal properties with the signal properties of the database, thus, identifying tissue types or other tissue components in vivo and in real-time.

Classification trees are used to solve problems in areas as diverse as target marketing, fraud detection, pattern recognition, computer vision, and medical diagnosis. In many applications, classification trees are carefully designed once but then applied to many data sets to provide automated classifications. This approach is used to create validated classifiers for tissue classification in mammography and intravascular ultrasound diagnostic procedures. While training the classifier is done offline, tree evaluation of each patient's data in these applications is an on-line algorithm where a user waits for a classification to be performed on many, many samples. Time spent waiting for this evaluation consumes valuable procedure room equipment and personnel. Performance requirements only increase when single images are replaced by moving video for computer vision applications, as in robotic navigation. In this environment, many classifications are needed in real-time to compute and affect a timely response. Thus the need for high-performance on-line evaluation of classification trees ranges from beneficial to absolutely necessary.

SUMMARY

Figure 5:
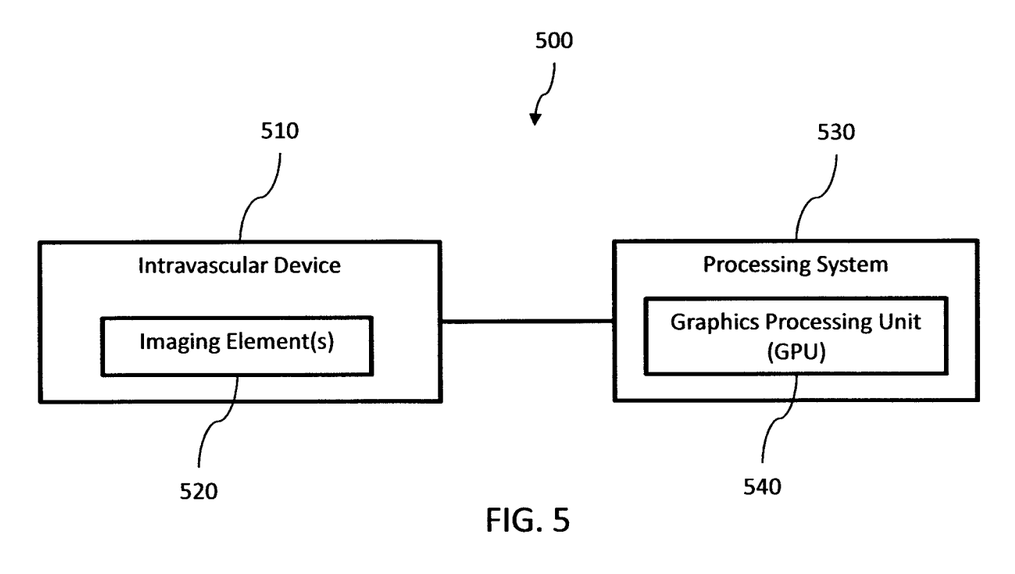
FIG. 5 is a diagrammatic schematic view of an imaging system according to an aspect of the present disclosure.

Methods and devices for optimizing classification tree evaluation for online and real-time characterization of tissue using GPUs are disclosed that give a significant improvement in run time compared to data decomposition. The methods and devices use an approach to tree evaluation on massively parallel GPU architectures, namely CUDA, for virtual histology processing in an IVUS or OCT imaging system. In that regard, as shown in FIG. 5, the IVUS or OCT imaging system 500 typically includes an intravascular device 510 (e.g., guide wire or catheter) sized and shaped for insertion into human vessels, such as the vasculature, and a processing system 530 in communication with the intravascular device for processing data obtained by imaging element(s) 520 of the intravascular device (e.g., an ultrasound transducer, ultrasound transducer array, OCT imaging element, etc.). The processing system 530 can include a graphics processing unit (GPU) 540. The methods and devices of the present disclosure may be implemented in a wide variety of IVUS and OCT imaging systems, including those disclosed in U.S. Pat. Nos. 6,200,268; 6,381,350; 7,074,188; 7,175,597; 7,215,802; 7,359,554; 7,463,759; 7,627,156; 7,789,834; 7,874,990; 7,899,224; 7,927,275; 7,929,148; 7,940,969; and 7,978,916; and U.S. Patent Application Publication Nos. 2010/0220334; 2009/0043191; and 2009/0093980; each of which is hereby incorporated by reference in its entirety. The methods and devices use a parallel algorithm designed for single instruction, multiple data (SIMD) architectures commonly found in GPUs. Various optimizations and their effects are also disclosed.

Rather than treating the full evaluation of one sample as the atomic parallel task, we parallelize the evaluation of each node in the tree for a single sample then reduce the resulting path through the tree in parallel. This approach has some performance benefits on architectures where execution of parallel processors is not independent, as in SIMD machines. When the approach of the present disclosure is compared to the data decomposition used in previous work and to the best-known serial host algorithm, in the specific environment we examine, results for the decomposition method of the present disclosure show a 25% performance improvement over data decomposition. We also see that host memory bandwidth and data distribution is an important measurement consideration that can dominate the nuances of GPU performance gains in typical PC systems, and must be accounted for in any statement of speedup results.

BRIEF DESCRIPTION OF THE DRAWINGS

Embodiments of the present disclosure will be described hereafter in detail with particular reference to the drawings. Throughout this description, like elements, in whatever embodiment described, refer to common elements wherever referred to and referenced by the same reference number. The characteristics, attributes, functions, interrelations ascribed to a particular element in one location apply to that elements when referred to by the same reference number in another location unless specifically stated otherwise. All Figures are drawn for ease of explanation of the basic teachings of the present disclosure only; the extensions of the Figures with respect to number, position, relationship and dimensions of the parts to form the preferred embodiment will be explained or will be within the skill of the art after the following description has been read and understood. Further, the exact dimensions and dimensional proportions to conform to specific force, weight, strength and similar requirements will likewise be within the skill of the art after the following description has been read and understood.

DETAILED DESCRIPTION

In utilizing classification trees, the assignment of a class to a given sample from a dataset requires that the sample be evaluated at each decision point along its path from the root of the tree to its eventual terminal leaf. While it may seem that each decision must be made in series for that sample, we note that each sample's classification is independent of all other samples. This allows us to decompose the problem of classifying all samples in a dataset into the independent problems of classifying each sample, which can be done in parallel. This decomposition according to sample data (a data decomposition approach) makes a growing number of parallel computing architectures available to speedup tree evaluation.

There is a good deal of literature on parallelization of training algorithms used to create classification trees in a traditional parallel processing setting. Research on the tree evaluation problem, however, focuses on Graphics Processing Units (GPUs) as the implementation platform. GPUs are typically designed specifically for data parallel applications. As inexpensive, commodity hardware found on every standard PC, GPUs match the cost, size, and power requirements of the on-line tree evaluation problem setting more closely than traditional super computers. Such application of graphics hardware to generic problems has become known as General Purpose GPU (GPOPU) computing.

Initial attempts to apply GPGPU techniques to tree evaluation stored the tree as an array of nodes containing the decision criteria of that node and an index used to locate the next node. Subsequent node indices were computed without conditional branches to avoid their heavy performance penalties on most GPUs. The tree definition was passed to the GPU as a texture map used by a custom pixel shader. The shader consumed input feature data and combined it with the texture to produce a final value, the assigned class, for each pixel in parallel. This can be extended to evaluate random forests by concatenating multiple tree structures in the texture data and iterating over all trees.

Classification Trees

In evaluating a classification tree, we are given a set of records, called the dataset, and a full binary decision tree, called the classifier. Each record in the dataset contains several fields, called attributes or features. One of the attributes, the classifying attribute, indicates to which class the record belongs and is unknown. In the general case, attributes can be continuous, having (real) numerical values from an ordered domain, or categorical, representing values from an unordered set. The classifier is a predictive model created through a process known as training. In training, observations on a training set of records, each having a known classifying attribute, are used to build a tree such that each interior, or, decision, node uses a single attribute value test to partition the set of records recursively until the subset of records at a given node have a uniform class. Such nodes are encoded in the tree as leaf nodes. The evaluation of a dataset is complete when the trained classifier is used to determine to which leaf, and thereby which class, each record belongs.

There are several training algorithms for examining attributes and generating trees known to those skilled in the art. Accordingly, the particular algorithm used will not concern us here, so long as the resulting tree has the above properties. We examine trees where all attributes are continuous, a common occurrence in image segmentation. While we will look at real-valued attributes (approximated with floating point numbers), ordered discrete values behave very much the same. Categorical attributes require some modifications to the approach described herein, as would be understood by one skilled in the art. We will further assume that class values can be enumerated and put into one-to-one correspondence with the natural numbers. Evaluation will operate only on numbers, and any mapping to another representation for class values (e.g. to descriptive strings or pixel values) will be done outside the evaluation process.

CUDA GPUs

GPGPU computing has grown in popularity in recent years as a technique for improving performance for massively parallel applications, especially where visualization and images are concerned. Initially, generic parallel computing was achieved on GPUs by cleverly mapping the processing into the graphics domain using libraries such as OpenGL to perform primitive tasks. As demand for customized graphics processing grew, vendors began supporting domain-specific programming languages like GL Shading Language (GLSL), making the GPU's floating point units more available.

In recent years, GPGPU computing frameworks have made great strides in removing assumptions about the domain and providing a generic capability to be used in any application needing massive parallelization. Perhaps the leading such framework, NVIDIA's CUDA architecture, can add tens or hundreds of GigaFLOPs to a system's capability on a single adapter card.

This power can be brought to bear on generic problems with great ease of use. The programming environments for these devices, whether vendor-specific or the industry standard OpenCL, can be used with no reference to the graphics domain. These environments subset the C/C++[2] programming language and provide a set of keyword extensions to manage the generation of both device-specific code and host code from the same source file set. In this way, code written to run on the GPU, called a kernel, is invoked with something that feels very akin to a C function call.

CUDA Programming Model

The CUDA runtime executes kernels across many threads, or individual streams of instructions (usually for a single atomic parallel task), and manages the mechanics of scheduling in hardware. Threads are grouped into blocks as 1, 2, or 3 dimensional arrays with each thread having a unique identifying index in each dimension of the block. Further, blocks are grouped into a 1 or 2 dimensional grid, with each block again having an identifying index in the grid dimensions. Each kernel invocation is done over a single grid and gives the grid and block dimensions to use when launched. Threads within a block are allowed to synchronize and share memory, but no communication between blocks is allowed. Threads are scheduled and executed in 32-thread units called a warp, with some operations happening on a half-warp, or 16 threads. All threads have access to their local memory (registers and stack), the shared memory of their block, and a global memory common to the entire device. The host can read from and write data to global memory but not local or shared memory. The host is required to copy kernel input and output data to and from device global memory outside of the kernel execution.

A simple example helps to illustrate a typical kernel invocation. First, the host CPU copies the input data to the GPU device's global memory. Since the host and device address spaces are separate, the CUDA runtime provides the host with APIs to allocate storage in device space, copy memory between spaces, look up device space symbol addresses, etc. The host must also allocate device global memory to store the results of the computation. The host can then invoke the CUDA runtime to launch the kernel with certain grid and block dimensions. Arguments such as the input and output buffers in device space are passed in the invocation. The device allocates execution resources to the kernel grid and schedules threads to execute in warps. Each thread uses its block and thread indices to identify its associated portions of input and output data. It can then do thread-specific memory transfer to its own stack and registers. Once the input data is locally available, computation is done and output is stored in device global memory. When all threads have completed, the host is signaled and is then free to copy the results from device to host memory and deallocate buffers.

CUDA Hardware Architecture

Figure 1:
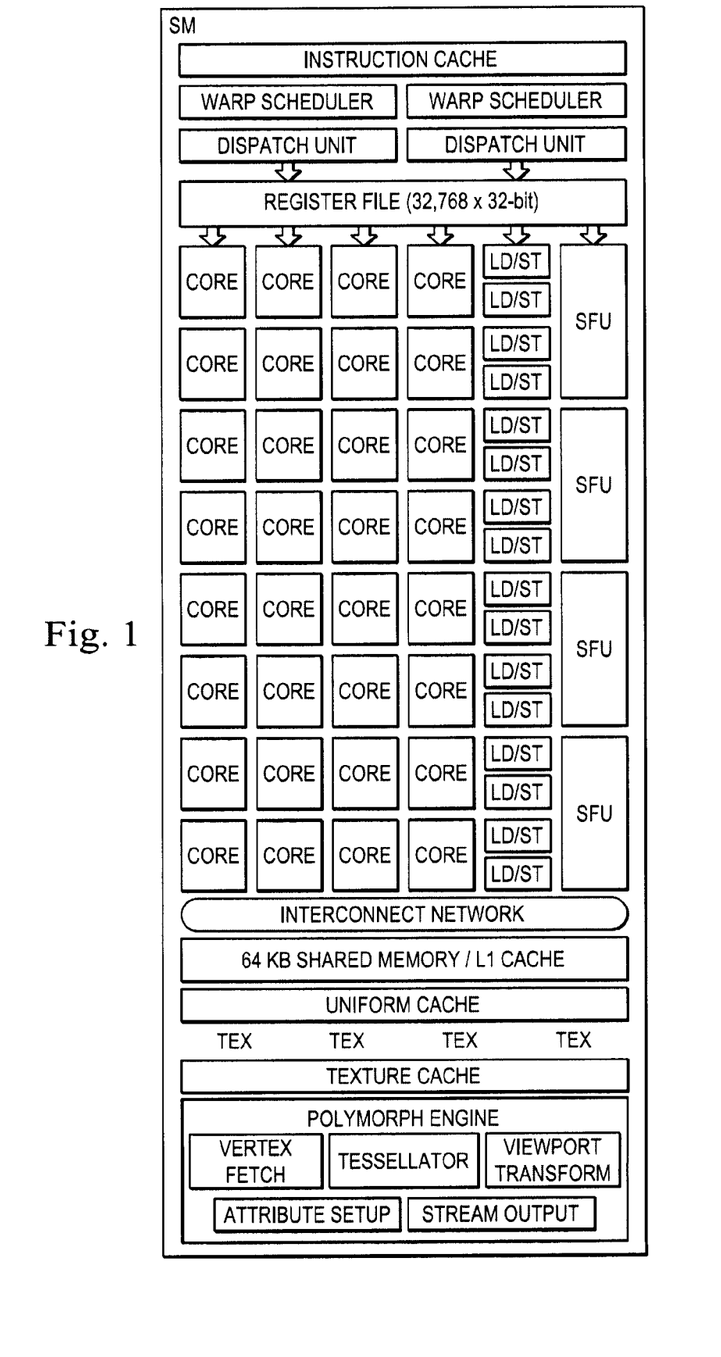
FIG. 1 is a schematic view of a streaming microprocessor capable of running the method of the present disclosure.
Figure 2A:
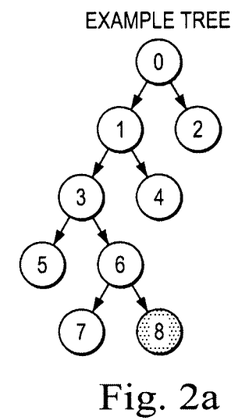
FIG. 2 is a diagram showing parallel tree path reduction.
Figure 2B:
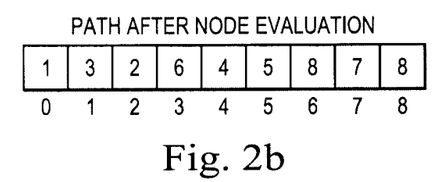
Figure 2C:
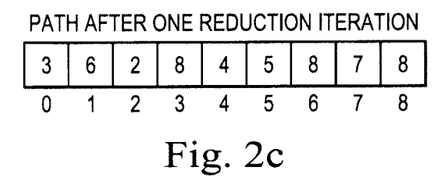
Figure 2D:
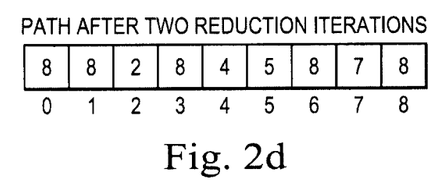

While an extensive discussion of CUDA architecture is unnecessary for one skilled in the art to understand and implement the embodiments of the present disclosure, some of the algorithm designs given herein are driven by certain qualities which bear discussion. The fundamental execution units of a CUDA device, called stream processors and known as cores, are arranged in N-way SIMD groups for some implementation-dependent N (usually 8, 32, or 48). These groups are combined with super function units (SFUs), instruction cache/decode logic, a register file, LI cache/shared memory, (usually 2) warp schedulers, and a network interconnect to form a streaming multiprocessor, or SM (FIG. 1). All threads in a block will be executed on the same SM, scheduled very efficiently by the hardware warp schedulers. When a warp is scheduled, all threads in that warp execute the same instruction, but have their own registers and stack. When some threads take conditional branches different from other threads, the warp executes the two paths in series until the paths merge. This is known as a divergent path, and can affect the kernel's performance substantially.

When a warp encounters a long-latency instruction (such as global memory access) it can be swapped for another warp in a small number of clocks. There is a limit to this capability, however, and the SM can only have so many blocks and threads resident at a time. This concept is known as occupancy, and can also affect the kernel's performance. Low occupancy means an SM has nothing to do during long latency instructions, so the SM is not fully utilized.

Finally, accessing global memory from an SM is an expensive operation, typically 100 times the cost of accessing local memory. In some CUDA implementations, accesses to global memory that meet certain requirements (such as contiguous access of 32, 64, or 128 bytes made in order by each core) can be coalesced into a single read, improving throughput. Later versions of CUDA hardware add L1 and even L2 cache, which mitigates the cost of non-coalesced reads.

Classification Tree Algorithms

The algorithm of the present disclosure is applied to virtual histology systems to correlate the backscatter data to known tissue types. It is natural to imagine an algorithm for evaluating a decision tree using a binary tree data structure and a depth-first traversal which, at each node, uses a conditional to evaluate whether the traversal should follow the left or right child of the node. Conditional statements, however, present problems for traditional CPUs (in the form of branch misprediction and pipeline flush) and GPUs (in the form of serialized divergent paths for SIMD warp execution.) This problem can be avoided by using a branchless tree traversal. In the present disclosure, branchless tree traversal is utilized for the base serial evaluation algorithm in some instances. A host implementation of this algorithm, as the best known serial algorithm, will be the reference by which speedup of parallel algorithms is determined.

Branchless Tree Evaluation

The evaluation problem can be stated as follow: given a dataset $\mathcal{D} = \{R: R=(r_1, \ldots, r_A), r_a \in \mathbb{R}\}$ with $|\mathcal{D}|=M$ and a full binary classification tree $\tau$ with a set of nodes $\mathcal{N} = \{n: n=(a_n, t_n, d_n^r, d_n^l, c_n)\}$ where:

$|\mathcal{N}|=N$ is the number of nodes in $\tau$ $1 \leq a_n \leq A$ is the index of attribute $r_{a_n}$ in each record R to be evaluated by node n $t_n \in \mathbb{R}$ is the threshold for attribute $r_{a_n}$ is used by node n $d_n^l \in \{\mathcal{N} \cup \emptyset\}$ is n's left descendant and recursively evaluates R when $r_{a_n} \leq t_n$ $d_n^r \in \{\mathcal{N} \cup \emptyset\}$ is n's right descendant and recursively evaluates R when $r_{a_n} > t_n$ $c_n \in \{C \cup \bot\}: C \subset \mathbb{N}$ s the set of possible class values} is $\bot$ when $(d_n^r \neq \emptyset \wedge d_n^l \neq \emptyset)$ or some $c \in C$ when $(d_n^r = \emptyset \wedge d_n^l = \emptyset)$ and having a root node $n_0$, assign to each $R \in \mathcal{D}$ a $c_R \in C$ by recursively evaluating R beginning at $n_0$.

To evaluate $\tau$ without branching, we first encode N in a breadth-first array of nodes.

Procedure 1 shows how each node is assigned an index i in the array breadthFirstTree to create a data structure describing the tree. Note that every right child has an index that is one more than the neighboring left child. Each node, then, need only store the index of its left child. To compute the index of the next node to evaluate, the node compares its attribute value r, against its threshold t, using the Boolean predicate "greater-than." If the result is false and encoded as 0, adding the result to the node's child index will yield the index of its left child, as desired. If the result is true encoded as a 1, adding it to the child index will yield the node's right child's index. While not strictly branchless due to the while loop, this technique does avoid any explicit conditional to compute the path to take at each decision node. The general algorithm is shown in Procedure 2.

Procedure 1 Breadth-first Encoding of Tree

```
 1:   breadthFirstTree= [ ]
 2:   Q=queue( )
 3:   push(Q, n_0)
 4:   i= 0
 5:   childIndex= 1
 6:   while Q not empty do
 7:       n = pop(Q)
 8:       node.attributeIndex = a_n
 9:       node.threshold = t_n
10:       node.classVal = c_n
11:       node.child = childIndex
12:       breadFirstTree[i] = node
13:       i = i + 1
14:       if d_n^l ≠ 0 then
15:           push(Q), d_n^l)
16:           childIndex = childIndex + 1
17:       if d_n^r ≠ 0 then
18:           push(Q, d_n^r)
19:           childIndex = childIndex + 1
```

| Procedure 2 Serial Tree Evaluation |
|---|
| 1:   Parameter: $\mathcal{D}$ |
| 2:   Parameter: breadthFirstTree[N] |
| 3:   Output: assignedClasses[$\lvert \mathcal{D} \rvert$] |
| 4:   for all R $\in \mathcal{D}$ do |
| 5:     i = 0 |
| 6:     while breadthFirstTree[i].classVal = $\perp$ do |
| 7:       a = breadthFirstTree[i].attributeIndex |
| 8:       t = breadthFirstTree[i].threshold |
| 9:       i = breadthFirstTree[i].childIndex + ($r_a > t$) |
| 10:     $c_R$ = breadthFirstTree[i].classVal |
| 11:     assignedClasses[R] = $c_R$ |

Data Decomposition

Procedure 2 is parallelized by data decomposition almost trivially, since each record is independent of the others. We can simply assign m records to p processors and have each loop only over m. The only additional work is to map the m records to the global dataset for the purposes of indexing into the input and output arrays. Procedure 3 shows the algorithm for each processor with indexing details for parameters D and assignedClasses. We use D (s ... t) to mean the subset of elements of D beginning at element s up to but not including element t. Here, we assume a shared memory architecture so that all processors have equal access to the parameter and output buffers. Knowing the index to a record R in D also gives the index to the corresponding assignedClasses value. The steps of making D, breadthFirstTree, and assigned-Classes available to each processor are omitted.

| Procedure 3 Data-Parallel Tree Evaluation |
|---|
| 1:   Parameter: $\mathcal{D}$ |
| 2:   Parameter: breadthFirstTree[N] |
| 3:   Parameter: m $\in \mathbb{N}$, the number of records for this processor to process |
| 4:   Parameter: p $\in \mathbb{N}$, this processor's rank |
| 5:   Output: assignedClasses[$\lvert \mathcal{D} \rvert$] |
| 6:   for all R $\in \mathcal{D}$ [m · p .. m(p + 1)) do |
| 7:     i = 0 |
| 8:     while breadthFirstTree[i].classVal = $\perp$ do |
| 9:       a = breadthFirstTree[i].attributeIndex |
| 10:       t = breadthFirstTree[i].threshold |
| 11:       i = breadthFirstTree[i].childIndex + ($r_a > t$) |
| 12:     $c_R$ = breadthFirstTree[i].classVal |
| 13:     assignedClasses[R] = $c_R$ |

Decomposition Method

While a data decomposition applies multiple processors to the evaluation problem very efficiently, the task of evaluating a single tree is still done serially. Once m is reduced to 1, no further processors can be applied to the problem usefully. Also, very deep and unbalanced trees may lead to asymmetries in the runtime between processors. In image segmentation, for instance, neighboring samples are expected to take similar paths through the tree and have almost uniform class values. By luck of the draw, some processor may be assigned m records that happen to be classified by the deepest node in the tree while others have records classified at the top of the tree. This leads to idle time in the "lucky" processors, and thereby, practical inefficiency. Further, adjacent records taking different paths leads to similar inefficiencies in SIND architectures like CUDA SMs or Intel's SSE instruction set.

The decomposition method of the present disclosure avoids the issues of divergent paths, irregular memory access patterns, idle time due to asymmetrical processing times, and to provide more uniform evaluation times needed in deterministic, real-time applications. We assign to each record a group of p processors, called a record group, such that p=N. If there are G such groups, the total number of processors becomes P=Gp. Within the group, each node n of the tree is assigned to processor $p^n$. The first step of the algorithm is to evaluate all nodes in parallel. Each processor stores the child node index i determined by the node evaluation into a shared memory array, path, having one element for each processor. The second step is to reduce the path through the tree to the selected leaf node. This is done by having each processor copy the path value of its child node into its own element of path. That is, each node finds its successor's successor and adopts that as its own successor. We can then think of the path array as storing the eventual successor for each node, with the eventual successor of the root node being the terminal node for the record. This step must be done synchronously across all processors in the record group. Leaf nodes are specifically designed to always evaluate to themselves by setting their threshold to -oo and their child index to be their own index.

FIG. 2 shows an example tree and the path array after the initial node evaluation (2b), then after one (2c) and two (2d) steps of the parallel reduction phase. Note that for a tree of depth d, only $\Theta(\log_2 d)$ reduction steps are necessary for the root node to arrive at the terminal leafs index. When this occurs, the reduction terminates.

Procedure 4 gives the parallel algorithm, which handles indexing the dataset as before but now accounts for the specific record group g in the calculation as well as determining which node of the tree each processor is assigned to and setting up the shared variable path. To compute the dataset indices, we can follow the form of Procedure 3 but substitute g for p. Again, we assume a shared arrangement for the input dataset and the output assignedClasses where the indices in each array correspond naturally. We use the primitive barrier( ) to provide syncluonization on updates to path from within record group g.

| Procedure 4 Speculative Parallel Tree Evaluation |
|---|
| 1:   Parameter: $\mathcal{D}$ |
| 2:   Parameter: breadthFirstTree[N] |
| 3:   Parameter: m $\in \mathbb{N}$, the number of records for this record group to process |
| 4:   Parameter: g $\in \mathbb{N}$, the record group this processor belongs to |
| 5:   Parameter: $p_n \in \mathbb{N}$, this processor's rank in the record group |
| 6:   Output: assignedClasses[$\lvert \mathcal{D} \rvert$] |
| 7:   Shared Variable: path[N] |
| 8:   for all R $\subset \mathcal{D}$ [m · g .. m(g + 1)) do |
| 9:     a = breadthFirstTree[$p_n$].attributeIndex |
| 10:     t = breadthFirstTree[$p_n$].threshold |
| 11:     path[$p_n$] = breadthFirstTree[$p_n$].childIndex + ($r_a > t$) |
| 12:     barrier(g) |
| 13:     rootClass = breadthFirstTree[path[0]].classVal |
| 14:     while rootClass = $\perp$ do |
| 15:       path[$p_n$] = path[path[$p_n$]] |
| 16:       barrier(g) |
| 17:       rootClass = breadthFirstTree[path[0]].classVal |
| 18:     $c_R$ = rootClass |
| 19:     assignedClasses[R] = $c_R$ |

Alternate Embodiment of Decomposition Method

A few inefficiencies exist in Procedure 4. First, processors assigned to leaf nodes will always produce the same, known output, and so their assigned processors do no productive work. To avoid this waste, the path array can be initialized with the known, static results for all leaves. Processors will only be assigned to decision nodes such that $0 \leq p_n < (N-1)/2$, the number of internal nodes in a full binary tree. This means, however, that mapping processors in a record group to tree nodes is no longer a simple, sequential operation. A tree-specific look-up table can accommodate this. As the record group processes, each processor will modify only the element of path it is assigned to.

Second, if the tree reduction is viewed probabilistically, we see that most records will end up at some leaf between levels 1 and d of the tree, averaging to some $d_t$, for the dataset. Checking the while condition on line 14 of Procedure 4 for all levels $d_r < d_\mu$ leads to an expected inefficiency. If $d_\mu$ is known or can be determined experimentally for the tree, reducing $d_\mu$ levels in a single while loop pass can provide an average case performance enhancement by reducing loop iterations and the number of barrier operations required.

Procedure 5 gives the improved parallel algorithm for decomposition method of the present disclosure. We add the static paths for the leafs of the tree on line 3, and use that to initialize the path array in parallel on line 10. Each processor must now initialize two elements of path since there are only processors for the internal nodes. We also add the processor-node map on line 4, which records the node index i assigned to each processor. Line 20 shows the concept of multiple reductions per loop, though the optimal implementation will be tree-specific.

---

Procedure 5 Speculative Parallel Tree Evaluation

1: Parameter: $\mathcal{D}$
2: Parameter: breadthFirstTree[N]
3: Parameter: leafPaths[N]
4: Parameter: processorNodeMap[(N − 1)/2]
5: Parameter: m ∈ $\mathbb{N}$, the number of records for this record group to process
6: Parameter: g ∈ $\mathbb{N}$, the record group this processor belongs to
7: Parameter: $p_n$ ∈ $\mathbb{N}$, this processor's rank in the record group
8: Output: assignedClasses[|$\mathcal{D}$|]
9: Shared Variable: path[N]
10: path[$2p_n$] = leafPaths[$2p_n$]
11: path[$2p_n$ + 1] = leafPaths[$2p_n$ + 1]
12: i = processorNodeMap[$p_n$]
13: for all R ∈ $\mathcal{D}$ [m · g .. m(g + 1)) do
14:     a = breadthFirstTree[i].attributeIndex
15:     t = breadthFirstTree[i].threshold
16:     path[i] = breadthFirstTree[i].childIndex + ($r_a$ > t)
17:     barrier(g)
18:     rootClass = breadthFirstTree[path[0]].classVal
19:     while rootClass = ⊥ do
20:         path[i] = path[path[path[i]]]
21:         barrier(g)
22:         rootClass = breadthFirstTree[path[0]].classVal
23:     $c_R$ = rootClass
24:     assignedClasses[R] = $c_R$

---

Management and Tuning of Parallel Algorithms

Some management work is required for each algorithm in the sections above that is well within the ability of those skilled in the art and consequently is omitted for brevity and to preserve generality. This includes making the buffers for 3E), assignedClasses, breadthFirstTree and any of the other necessary symbols available to all the parallel processors for each algorithm. The mechanism for sharing these buffers depends on the programming environment used. Also, selection of optimal values for G and m given P, N, M, and the available execution hardware architecture is critical but entirely implementation dependent.

Analysis of Evaluation Algorithms

We now analyze the asymptotic behavior of these general algorithms assuming a traditional parallel processing setting of independent processors connected via shared memory. We perform an average case run time analysis by assigning $d_\mu$ to be the average depth of the tree traversed by the records in the dataset. This can be determined if the entire dataset is known a priori, or can be statistically estimated given a significant sample size, such as the training set. The serial runtime for Procedure 2 for M records is given by $$T_2 = M d_\mu (t_e + t_c)$$

where $t_e$ is the time to evaluate a node's attribute against its threshold and $t_c$ is the time to compare the new node's class value to ⊥. We also refer to $t_n = t_e + t_c$ as the time needed to evaluate a node.

The run time for Procedure 3 is a function of P, the total number of processors applied, and is given by $$T_3(P) = \frac{M}{P} d_\mu (t_e + t_c) + t_i + t_s(M)$$

where each processor classifies M/P records, $t_i$ is the time needed to compute the index in D assigned to the each processor, and $t_s(M)$ is the time needed to transmit M records on the shared memory machine for processing. We can then examine the speedup of Procedure 3 as $$S_3(P) = \frac{T_2}{T_3(P)} = \frac{M d_\mu (t_e + t_c)}{\frac{M}{P} d_\mu (t_e + t_c) + t_i + t_s(M)}$$

$$= \frac{P}{1 + \frac{P(t_i + t_s(M))}{M d_\mu (t_e + t_c)}}$$

If we assume $t_s(M) = \sigma M + \gamma$ for some σ, γ and we ignore γ and t as small constants, then this simplifies asymptotically to $$S_3(P) \approx \frac{P}{1 + \frac{P\sigma}{d_\mu t_n}}$$

which suggests the speedup will be decided by the relative performance of the memory copy and the serial node processing time. If they are very similar, we would not expect much speedup. If memory copies are very fast compared to node processing, some benefit may be had. Likewise for the efficiency, given by $$E_3(P) = \frac{S_3(P)}{P} \approx \frac{1}{1 + \frac{P\sigma}{d_\mu t_n}}$$

we expect good results only when copy time is much less than processing time.

For Procedure 5, the analysis is a bit more involved. If each group of processors is assigned m=M/G records for G groups of p processors such that P=Gp, the parallel runtime is given by $$T_5(P) = \frac{Mp}{P}(t_e + (\log_2 d_\mu) t_c) + t_i + t_s(M)$$

and the speedup is $$S_5(P) = \frac{T_2}{T_5(P)} = \frac{M d_\mu (t_e + t_c)}{\frac{M_p}{P}(t_e + (\log_2 d_\mu) t_c) + t_i + t_s(M)}$$

$$= \frac{P}{\frac{p(t_e + (\log_2 d_\mu) t_c)}{d_\mu (t_e \mid t_c)} + \frac{P(t_i + t_s(M))}{M d_\mu (t_e \mid t_c)}}$$

with efficiency $$E_5(P) = \frac{S_5(P)}{P} \approx \frac{1}{\frac{p(t_e + (\log_2 d_\mu) t_c)}{d_\mu (t_e + t_c)} + \frac{P_\sigma}{d_\mu t_n}}$$

Making the same assumptions about $t_s(M)$, $t_i$, and $\gamma$, $S_5(P)$ simplifies asymptotically to $$S_5(P) \approx \frac{P}{\frac{p(t_e + (\log_2 d_\mu) t_c)}{d_\mu (t_p + t_r)} + \frac{P_\sigma}{d_\mu t_n}}$$

For the values of P and $d_\mu$, we examine, this should not be very different from $S_3(P)$. However, these equations allow us to examine when $S_5(P) > S_3(P)$, which occurs when $$\frac{p(t_e + (\log_2 d_\mu) t_c)}{d_\mu (t_e + t_c)} < 1, \text{ or}$$

$$p(t_e + (\log_2 d_\mu) t_c) < d_\mu (t_e + t_c)$$

$$p < \frac{d_\mu (t_e + t_c)}{t_e + (\log_2 d_\mu) t_c}$$

If we further assume $t_e$ and $t_c$ are roughly equivalent operations (both being comparisons) and each taking time t, we can simplify this to $$p < \frac{2 t d_\mu}{t(1 + \log_2 d_\mu)}$$

$$p < \frac{2 d_\mu}{1 + \log_2 d_\mu}$$

For practical values of $d_\mu$, the slope of the graph of 1 is around ⅓. Since the number of decision nodes grows faster than the average depth (at a rate dependent on the balancing of the tree), we should not expect a great speedup from Procedure 5 for any but the most shallow trees.

Experiments on Parallel Classification Tree Algorithms

The preceding analysis assumes each parallel node execution is independent from the others. In GPUs, particularly CUDA architecture, this is not the case. We expect to see a performance benefit due to local caching of neighboring records read from global memory in bursts, the SIMD coupling of execution nodes evaluated in parallel for each sample, having multiple SIMD groups resident and quickly switched to on the chosen hardware, and other such concerns. These are not general concerns but are specific to a particular hardware architecture. In this setting, it makes sense to pursue more specific analysis by experimentation. The following sections detail experiments done on the CUDA platform with runtime as the metric of performance.

Problem Selection

We selected the Image Segmentation dataset from UC Irvine's Machine Learning Repository as an evaluation problem representative of tasks in medical imaging or computer vision. This data set consists of 2310 records for training and an additional 2099 for testing. Each record consists of 19 real-valued attributes of a 3×3 pixel neighborhood and corresponds to one of 7 discrete classes.

Figure 3:
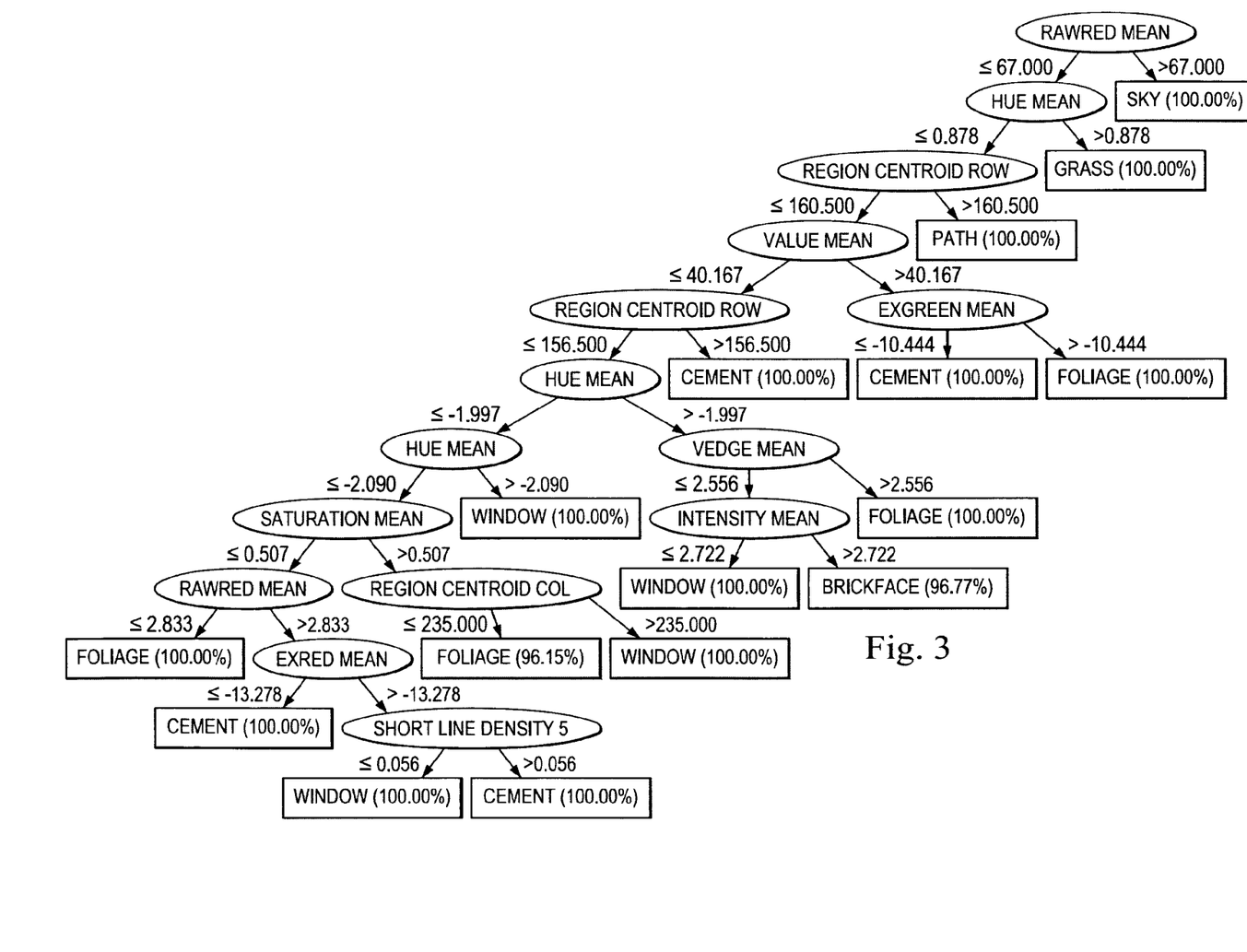
FIG. 3 is a diagram showing an experimental classification tree according to the present disclosure.

To generate a classifier based on this dataset, we used the Orange component-based machine learning library. This library provides Python bindings to a mature C++ machine learning library. We wrote a Python script to read the training set, train a classification tree, and generate C++ source code which encodes that tree according to Procedure 1. The resulting tree is shown schematically in FIG. 3. This tree has N=31 nodes, 16 leaves, and a depth of 11.

Further, the script also combined the training set and the test set of records into a single table, then repeatedly randomized and output the records as C++ source code for easy inclusion in our test program. This process was repeated until 16,384 C++ records were generated. This set can be duplicated four times at runtime to create a dataset having 65,536 records, representing an image of 256×256 pixels.

Experiment Setup—Machine Configuration

Experiments were performed on a Dell Optiplex 780 with an Intel Core2 Duo E8600 CPU running at 3.33 GHz, 4 GB RAM, and the Windows 7 64-bit operating system. An NVIDIA Quadro 2000 GPU card was added with 1 GB of 128-bit RAM with a bandwidth of 41.6 GB/s and 192 CUDA cores in 4 SMs of 48 cores each with a 1.25 GHz processor clock. Software on the system included the NVIDIA driver version 263.06 and the CUDA 3.2.1 mntime Dll version 8.17.12.6303. All compilation was done with Microsoft Visual Studio 2008 and the CUDA 3.2 Development Toolkit, with project files generated by CMake version 2.8.3.

Tests Conducted

We created a program which, after building a dataset of 65,536 records, ran three tree evaluation functions 500 times each on the full dataset. For each function call, the Windows high performance counter was started before and stopped after the call and the delta time was accumulated. This is called the outer time for the algorithm. For those functions using a CUDA kernel, a similar inner time was collected around just the kernel invocation and excluded any time for memory copy to or from the GPU. During the kernel runtime, the host CPU was made to wait until the kernel completed. The three functions evaluated were as follows:

EvalTree:

This function implements Procedure 2, a serial algorithm running on the host. Note that this function records no inner time and that the outer time does not include any memory copies since none are required for the host to evaluate the dataset.

EvalTreeBySample( ):

This is the data parallel algorithm given in Procedure 3. This function is written in CUDA C, and performs a host-to-device copy of the dataset and the tree definition before invoking the kernel. The grid is formed of 512 blocks having 128 threads each, all single-dimensioned. Only one record is evaluated per thread (i.e. m=1.) For this function (and all other CUDA functions), the tree is copied to device constant memory for cacheing purposes. When the kernel completes, the host copies the resulting class assignments back to host memory and frees all device resources.

EvalTreeByNode( ):

This function fully implements the improved speculative algorithm corresponding to Procedure 5 with the following considerations: constant memory is used for the processor-node map and static leaf path buffers in addition to the tree definition; multiple reductions (specifically 2, determined empirically) are performed per iteration of the path reduction loop; and the explicit barrier( ) operations are omitted since each thread executes synchronously within a warp. The shared memory path variable is initialized from the static leaf buffer only once at kernel invocation. This is safe since leaves never change and internal nodes are re-initialized by the node evaluation step done for each record. The grid is set to 128 blocks of 16×16 threads. Thus each block processes 16 record groups in parallel, each record group using p=16 threads (a half-warp) to evaluate a record. Note that there are only 15 internal nodes in the tree, so one thread is idle per record group (assigned to a phantom node). With 128×16 record groups, each must process m=32 records per group to cover 65,536 records exactly. Having thread geometry exactly match data size allows us to remove checks for over-sized grids—a non-portable practice but one with a noticeable performance effect. Data copies to and from the device were the same as in EvalTree By Sample ( ).

After each CUDA function call, the returned buffer of class assignments was compared to the results obtained using the serial algorithm, and any discrepancies were reported. None were found.

The entire program also ran with the CUDA profiler enabled. This facility captures device timestamps and other metrics resulting from the program execution.

Results

The program output giving the outer and inner times along with related statistics is summarized in Table 1. Most notable is that the serial evaluation on the host is twice as fast as the fastest parallel GPU version. This is surprising but perhaps a bit misleading, since no great pains were taken to optimize the memory copy tasks, all done in series. Pinning and aligning the host memory buffers and overlapping copies with computation are viable techniques to boost performance for this problem.

(FIG. 4), though uniformly lower than those measurable outside of the CUDA driver. The GPU times confirm a ~25% improvement in kernel times of 353.47 µs vs 485.17 µs. The time in the graph for "memcpyHtoD" shows the copy time of the data set and tree definitions (two invocations per execution) for both CUDA functions over 500 iterations each. Adding this and the "memcpyDtoH" time to each of the kernel times gives the outer time for each function, less time taken by the host to allocate/free buffers and manage the function calls.

The profiler data also shows EvalTreeByNode taking an average of 4373 divergent branches across all threads due to the half-warp scheduling, whereas EvalTreeBySample shows 3530 across all threads, as each thread in a warp will iterate through the tree a different number of times. EvalTreeByNode had a global cache read hit rate of 70%, while EvalTreeBySample had a hit rate of only 31%.

With fewer threads per block, EvalTreeBySample encounters the limit on active blocks, leaving the achieved occupancy rate at 66%. EvalTreeByNode avoids this issue and achieves 100% occupancy. This increases the number of global memory requests for record data that can be active, and thus enhances the effect of latency hiding by the warp scheduler. This can be seen in the global memory write throughput of 0.643 GB/s versus 4.68 GB/s. Read throughputs are roughly equal at 14 GB/s (due to caching), giving overall global memory throughputs of 15.43 GB/s for EvalTreeBySample and 19.41 GB/s for EvalTreeByNode.

The decomposition algorithm for parallel classification tree evaluation disclosed herein surpasses the performance of a data decomposition parallel algorithm on the CUDA platform. When ignoring the common, serial algorithm setup processing, the approach of the present disclosure is 25% faster than the data parallel approach in our particular problem instance. This demonstrates how different parallel decomposition techniques can maximize the advantages of a given platform. In a SIMD environment, we see that decomposition method of the present disclosure into many time-uniform tasks can have a helpful effect even at the cost of less

TABLE 1

Outer and Inner Times According to High-Performance Counter

| | | | | | | | | |
|---|---|---|---|---|---|---|---|---|
| EvalTree By Sample | 3907.57 | 3794.19 | 4741.2 | 71.2049 | 538.235 | 525.705 | 769.309 | 15.3554 |
| EvalTree By Node | 3785.29 | 3685.17 | 4677.76 | 87.0612 | 404.466 | 394.817 | 432.698 | 10.9616 |

| Algorithm | Average Outer Time (µs) | Min Outer Time (µs) | Max Outer Time (µs) | Std Dev | Average Inner Time (µs) | Min Inner Time (µs) | Max Inner Time (µs) | Std Dev |
|---|---|---|---|---|---|---|---|---|
| EvalTree (Host) | 1914.16 | 1900.48 | 2343.65 | 43.481 | N/A | N/A | N/A | N/A |

In our main result, comparing the inner times for kernel execution we see a roughly 25% performance increase in EvalTreeByNode over EvalTreeBySample. Further experiments on EvalTreeByNode showed that inclusion of a conditional for checking an over-sized warp increased runtime to roughly the same as EvalTreeBySample. With m=1, timings were again roughly equal, showing that the expense of the initial load of static paths and the processor-node map are amortized over multiple record iterations. Values for m>32 (with related block resizing) showed no significant benefit. This and other experiments suggests that CUDA thread scheduling is as efficient as iterating in a for loop.

Figure 4:
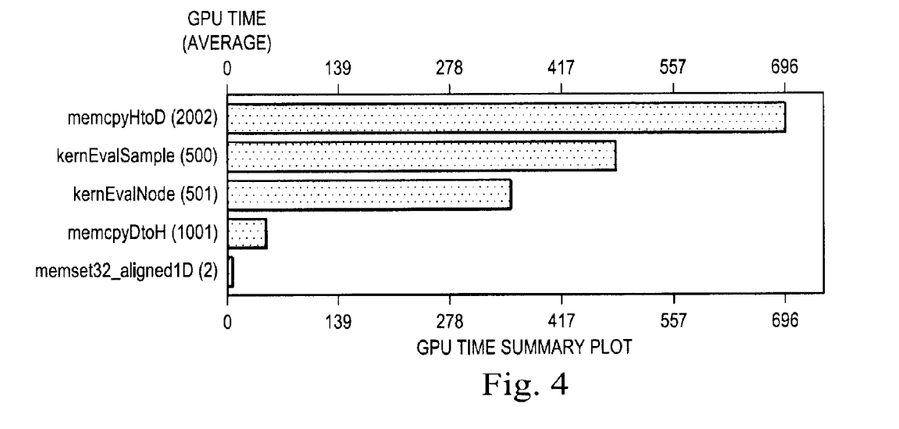
FIG. 4 is a time summary plot showing the average timings taken by CUDA runtime over 500 executions (μs).

Examination of the CUDA profiler output shows similar results for kernel timings efficient hardware utilization. We also see a good example of implementation results deviating from asymptotic theoretical analysis. This is most true when fundamental assumptions, such as independent execution units, do not hold in the implementation as is the case here. Ultimately, the best performance requires a careful balance of machine and algorithm for a specific problem.

Additionally, we've seen that measurement techniques that do not include the entire program overhead of distributing data or that compare different algorithms can lead to confusing results. Some of the differences suggest that a branchless evaluation algorithm ought to be used as the best known serial algorithm for speedup comparisons.

In a further embodiment of the present disclosure, application of the embodiments described herein to very large trees can be achieved by evaluating only a small "window" on the tree, starting at a root node and evaluating only the next few levels. Once reduced, the resulting node would then become the root of the next window and the process repeated. This approach may be useful in overcoming SIMD concurrency limits (such as on a vectored processor) or the exponential growth of memory demand for deeper and deeper levels of the tree.

Incorporated herein by reference in their entirety are the following:

Paul Baumstarck. GPU parallel processing for fast robotic perception. Thesis, Engineer's degree, Stanford University, December 2009.

Yael Ben-Haim and Elad Tom-Tov. A streaming parallel decision tree algorithm. J. Mach. Learn. Res., 11:849-872, March 2010.

Ruoming Jin and Gagan Agrawal. Shared memory parallelization of decision tree construction using a general data mining middleware. In Proceedings of the 8$^{th}$ International Euro-Par Conference on Parallel Processing, Euro-Par '02, pages 346-354, London, UK, 2002. Springer-Verlag.

Mahesh V. Joshi, George Karypis, and Vipin Kumar. Scalparc: A new scalable and efficient parallel classification algorithm for mining large datasets. In Proc. of the International Parallel Processing Symposium, pages 573-579, 1998.

David B. Kirk and Wen-mei W. Hwu. Programming Massively Parallel Processors: A Hands-on Approach. Morgan Kaufmann, 1st edition, February 2010.

Manish Mehta, Rakesh Agrawal, and Jorma Rissanen. Sliq: A fast scalable classifier for data mining. In Proc. of the Fifth International Conference on Extending Database Technology (EDBT), pages 18-32, Avignon, France, March 1996.

A. Nair, B. Kuban, E. Tuzcu, P. Schoenhagen, S. Nissen, and D. Vince. Coronary plaque classification with intravascular ultrasound radiofrequency data analysis. Circulation, 106: 2200-2206, October 2002.

Arnau Oliver and Jordi Freixenet. Automatic classification of breast density. In IEEE International Conference on Image Processing, pages 1258-1261, 2005.

Jason Sanders and Edward Kandrot. CUDA by Example: An Introduction to General-Purpose GPU Programming. Addison-Wesley Professional, 1st edition, July 2010.

John Shafer, Rakeeh Agrawal, and Manish Mehta. Sprint: A scalable parallel classifier for data mining. In Proceedings of the 22nd International Conference on Very Large Databases (VLDB), pages 544-555. Morgan Kaufmann, September 1996.

Toby Sharp. Implementing decision trees and forests on a gpu. In European Conference on Computer Vision (ECCV) 2008, volume 5305 of Lecture Notes in Computer Science, pages 595-608. Springer, 2008.

D. Steinkraus, I. Buck, and P. Y. Simard. Using gpus for machine learning algorithms. In Document Analysis and Recognition, 2005. Proceedings. Eighth International Conference on, pages 1115-1120 Vol. 2, Aug.-1 Sep. 2005.

Mohammed J. Zaki, Ching-Tien Ho, and Rakesh Agrawal. Parallel classification for data mining on shared-memory multiprocessors. Data Engineering, International Conference on, 0:198, 1999.

The present disclosure has been described in connection with certain embodiments, combinations, configurations and relative dimensions. It is to be understood, however, that the description given herein has been given for the purpose of explaining and illustrating the embodiments and are not intended to limit the scope of the invention. For example, even though the present disclosure has been described primarily as being used with virtual histology in an NUS imaging system, both in side and forward looking NUS imaging systems, the embodiments of the present disclosure are also suitable for use in an optical coherence tomography (OCT) imaging system. In addition, it is clear than an almost infinite number of minor variations to the form and function of the disclosed embodiments could be made and also still be within the scope of the present disclosure. Consequently, it is not intended that the invention be limited to the specific embodiments and variants of the invention disclosed. It is to be further understood that changes and modifications to the descriptions given herein will occur to those skilled in the art. Therefore, the scope of the invention should be limited only by the scope of the claims.

The invention claimed is:

1. A method of identifying components within a vascular object from a signal, the method comprising:
    transmitting a signal within a selected region of the vascular object and collecting a backscatter signal reflected from the vascular object;
    reconstructing an image of the selected region from the backscatter signal;
    preparing a histology image of the selected region of the vascular object, the histology image distinguishing different components of the vascular object;
    selecting a region of interest from the histology image, the region of interest representing one component from the different components of the vascular object and being at a coordinate location on the histology image;
    mapping the coordinate location to a location on the image corresponding to the coordinate location;
    translating the location on the image to a signal portion in the backscatter signal corresponding to the location, the signal portion representing a signal signature of the one component of the vascular object; and
    correlating the signal signature to the one component using a classification tree scheme using a graphic processing unit (GPU), wherein using the classification tree scheme includes performing data decomposition of a sample of the signal portion by evaluating in parallel all nodes in a tree associated with the sample of the signal portion and thereafter synchronously reducing a path through the tree, the path being defined by the evaluation of all nodes in the tree, wherein evaluating all nodes in the tree includes implementing branchless tree traversal, wherein reducing the path through the tree includes providing a static path for each of a subset of all nodes in the tree, and wherein reducing the path through the tree includes reducing the path a plurality of times per computational loop, wherein the correlating further comprises generating a processor-node map that correlates a subdivision of the GPU with an index of a node of the tree associated with the sample of the signal portion.

2. The method of claim 1 wherein the signal is an intravascular ultrasound signal.

3. The method of claim 1 wherein the signal is an optical coherence tomography signal.

4. The method of claim 2, wherein the intravascular ultrasound signal is transmitted from at least one of: a single transducer element and an array of ultrasound transducers.

5. The method of claim 1, wherein the GPU comprises a single instruction, multiple data (SIMD) architecture.

6. The method of claim 1, wherein the GPU comprises a plurality of streaming multiprocessors.

7. A device for identifying components within a vascular object from a signal comprising:

a transducer for transmitting a signal within a selected region of the vascular object and collecting a backscatter signal reflected from the vascular object; and a computing system including a graphics processing unit (GPU), the computing system configured to:

reconstruct an image of the selected region from the backscatter signal;

prepare a histology image of the selected region of the vascular object, the histology image distinguishing different components of the vascular object;

select a region of interest from the histology image, the region of interest representing one component from the different components of the vascular object and being at a coordinate location on the histology image;

map the coordinate location to a location on the image corresponding to the coordinate location;

translate the location on the image to a signal portion in the backscatter signal corresponding to the location, the signal portion representing a signal signature of the one component of the vascular object; and correlate the signal signature to the one component using a classification tree scheme using the GPU, wherein the computing system is further configured to use the GPU to perform data decomposition of a sample of the signal portion by evaluating in parallel all nodes in a tree associated with the sample of the signal portion with branchless tree traversal and thereafter synchronously reducing a path through the tree, the path being defined by the evaluation of all nodes in the tree.

8. The device of claim 7, wherein the transducer comprises at least one of: a single transducer element and an array of ultrasound transducers.

9. The device of claim 7, wherein the GPU comprises a single instruction, multiple data (SIMD) architecture.

10. The device of claim 7, wherein the computing system is configured to use the classification tree scheme to implement a static path through the tree associated with the sample of the signal portion for each of a subset of all nodes in the tree.

11. The device of claim 7, wherein the computing system is configured to use the classification tree scheme to implement a processor-node map that correlates a subdivision of the GPU with an index of a node of the tree associated with the sample of the signal portion.

12. The device of claim 7, wherein the computing system is configured to use the classification tree scheme to reduce a path through the tree multiple times per computational loop.

13. The device of claim 7, wherein the GPU comprises a plurality of streaming multiprocessors.

14. A method of identifying components within a vascular object from a signal, the method comprising:

transmitting a signal within a selected region of the vascular object and collecting a backscatter signal reflected from the vascular object;

reconstructing an image of the selected region from the backscatter signal;

preparing a histology image of the selected region of the vascular object, the histology image distinguishing different components of the vascular object;

selecting a region of interest from the histology image, the region of interest representing one component from the different components of the vascular object and being at a coordinate location on the histology image;

mapping the coordinate location to a location on the image corresponding to the coordinate location;

translating the location on the image to a signal portion in the backscatter signal corresponding to the location, the signal portion representing a signal signature of the one component of the vascular object; and correlating the signal signature to the one component using a classification tree scheme using a graphic processing unit (GPU), wherein using the classification tree scheme includes evaluating in parallel all nodes in a tree associated with a sample of the signal portion and thereafter synchronously reducing a path through the tree, the path being defined by the evaluation of all nodes in the tree.

15. The method of claim 14, wherein using the classification tree scheme includes implementing branchless tree traversal for the tree associated with the sample of the signal portion.

16. The method of claim 14, wherein using the classification tree scheme includes providing a static path through the tree associated with the sample of the signal portion for each of a subset of all nodes in the tree.

17. The method of claim 14, wherein using the classification tree scheme includes generating a processor-node map that correlates a subdivision of the GPU with an index of a node of the tree associated with the sample of the signal portion.

18. The method of claim 14, wherein using the classification tree scheme includes reducing a path through the tree multiple times per computational loop.

* * * * *